United States Patent
Spreiter et al.

(10) Patent No.: US 11,553,933 B2
(45) Date of Patent: Jan. 17, 2023

(54) SYSTEM AND METHOD FOR INSERTING AN INTRAMEDULLARY NAIL

(71) Applicant: DEPUY SYNTHES PRODUCTS, INC., Raynham, MA (US)

(72) Inventors: Gregor Spreiter, Solothurn (CH); Henri Défossez, Neuchatel (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 322 days.

(21) Appl. No.: 16/736,400

(22) Filed: Jan. 7, 2020

(65) Prior Publication Data
US 2021/0204966 A1    Jul. 8, 2021

(51) Int. Cl.
| *A61B 17/17* | (2006.01) |
| *A61B 17/72* | (2006.01) |
| *A61B 17/88* | (2006.01) |
| *A61B 17/86* | (2006.01) |

(52) U.S. Cl.
CPC .......... *A61B 17/1725* (2013.01); *A61B 17/72* (2013.01); *A61B 17/8891* (2013.01); *A61B 17/86* (2013.01)

(58) Field of Classification Search
CPC . A61B 17/1703; A61B 17/921; A61B 17/744; A61B 17/8897; A61B 17/90; A61B 17/1721; A61B 17/175; A61B 17/72; A61B 17/8891; A61B 17/1725; A61B 17/8615; A61B 17/8872; A61B 17/866; A61B 17/869; A61B 17/86; A61B 17/863; A61B 17/888; A61B 17/1717; A61B 2017/00469; A61B 2017/0092
See application file for complete search history.

(56) References Cited

U.S. PATENT DOCUMENTS

| 3,116,775 | A |  | 1/1964 | Russell |  |
| 5,766,174 | A | * | 6/1998 | Perry | A61B 17/1725 |
|  |  |  |  |  | 606/62 |
| 6,302,629 | B1 |  | 10/2001 | Hsiao |  |
| 7,056,162 | B2 |  | 6/2006 | Tournier et al. |  |
| 8,784,430 | B2 | * | 7/2014 | Kay | A61B 17/1725 |
|  |  |  |  |  | 606/104 |
| 8,985,926 | B2 |  | 3/2015 | Hamano et al. |  |
| 9,022,709 | B2 |  | 5/2015 | Benzing |  |
| 9,155,582 | B2 | * | 10/2015 | Felder | A61B 17/72 |
| 9,995,334 | B2 |  | 6/2018 | Matsubayashi |  |
| 10,060,465 | B2 |  | 8/2018 | Hwang et al. |  |
| 2007/0123873 | A1 | * | 5/2007 | Czartoski | A61B 17/7233 |
|  |  |  |  |  | 606/62 |
| 2009/0136317 | A1 |  | 5/2009 | Chen |  |
| 2009/0297292 | A1 |  | 12/2009 | Katayama et al. |  |

(Continued)

Primary Examiner — Julianna N Harvey
(74) Attorney, Agent, or Firm — Fay Kaplun & Marcin, LLP

(57) ABSTRACT

An intramedullary (IM) nail insertion assembly includes an IM nail extending longitudinally from a proximal end to a distal end. A proximal portion of the IM nail has an internal threading. The IM nail insertion assembly also includes a connecting screw extending longitudinally from a proximal end to a distal end. A distal portion of the connecting screw has an external threading for engaging the internal threading of the TM nail. One of the proximal portion of the IM nail and the distal portion of the connecting screw has a feature to resist a disengagement of the proximal portion from the distal portion.

20 Claims, 5 Drawing Sheets

(56) References Cited

U.S. PATENT DOCUMENTS

| | | | |
|---|---|---|---|
| 2011/0288598 A1* | 11/2011 | Moed | A61B 17/8625 |
| | | | 606/303 |
| 2013/0330146 A1 | 12/2013 | Harada et al. | |
| 2014/0017027 A1 | 1/2014 | Benzing | |
| 2014/0105705 A1 | 4/2014 | Hamano et al. | |
| 2014/0369786 A1 | 12/2014 | Hsieh | |
| 2015/0257800 A1* | 9/2015 | Harshman | A61B 17/1717 |
| | | | 606/62 |
| 2015/0285293 A1 | 10/2015 | Kawakami | |
| 2016/0115990 A1 | 4/2016 | Xu | |
| 2016/0131176 A1 | 5/2016 | Xu | |
| 2016/0153486 A1 | 6/2016 | Xu | |
| 2017/0105774 A1* | 4/2017 | Prien | A61B 17/861 |
| 2017/0219003 A1 | 8/2017 | Hwang et al. | |
| 2018/0231048 A1 | 8/2018 | Liu | |
| 2018/0368894 A1* | 12/2018 | Wieland | A61B 17/8042 |
| 2019/0017532 A1 | 1/2019 | Yue | |
| 2019/0063486 A1 | 2/2019 | Kim | |
| 2019/0234446 A1 | 8/2019 | Chang | |
| 2019/0242425 A1 | 8/2019 | Chen et al. | |
| 2019/0271351 A1 | 9/2019 | Yoon et al. | |

* cited by examiner

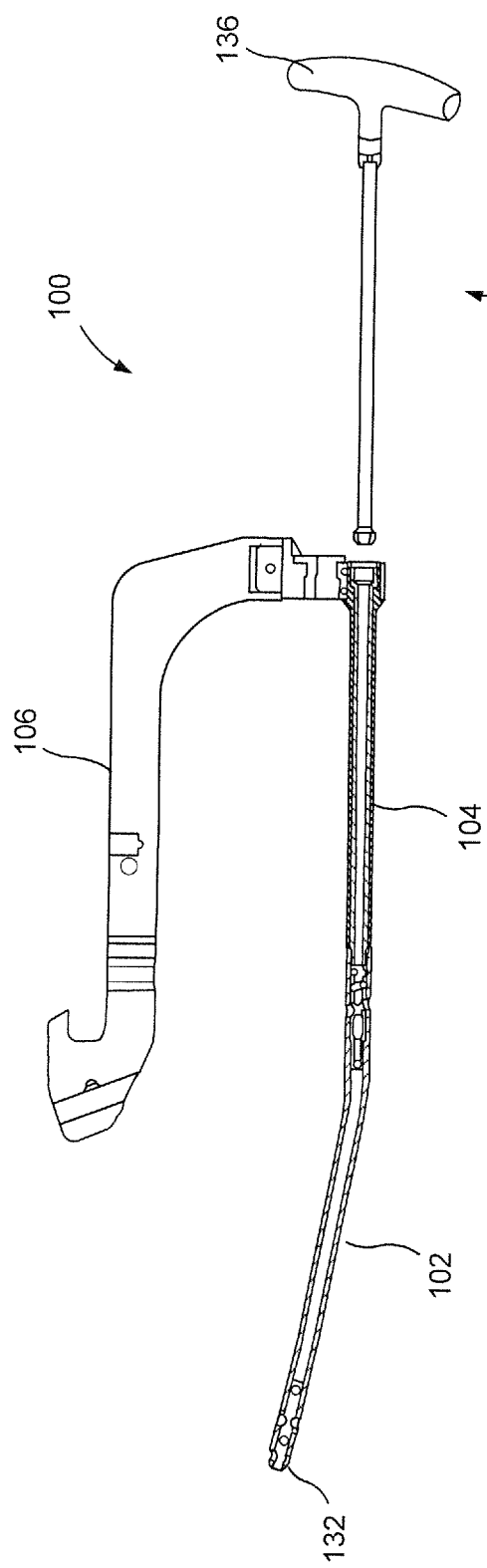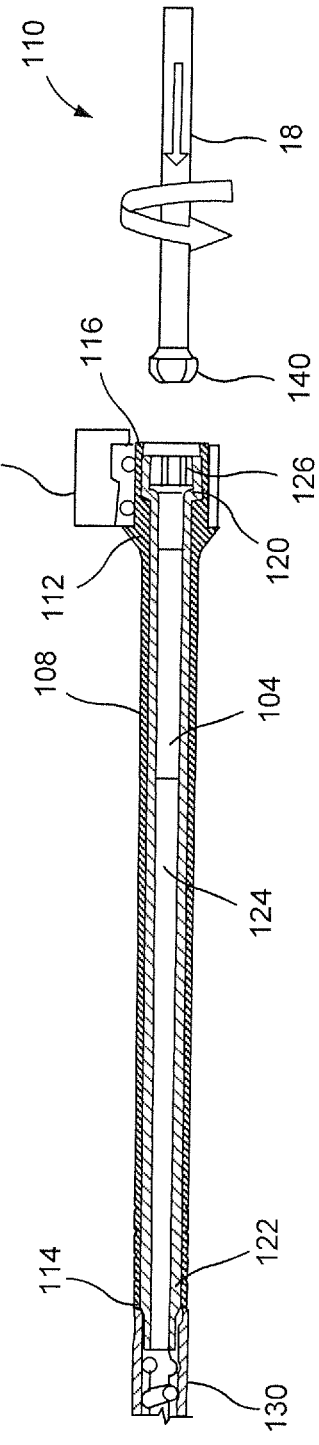
FIG. 1
FIG. 2

SYSTEM AND METHOD FOR INSERTING AN INTRAMEDULLARY NAIL

FIELD OF INVENTION

The present disclosure relates generally to a connecting screw, which attaches an intramedullary nail onto a device which enables insertion of the intramedullary nail, the connecting screw having features to resist disengagement or loosening during nail insertion.

BACKGROUND

A bone defect may be repaired by inserting a permanent nail or rod into the medullary canal of the bone. A connecting screw may be attached at one end to the intramedullary (IM) nail and a force applied to the opposing end of the connecting screw to insert the IM nail into the medullary canal. The connecting screw may loosen during the nail insertion procedure as a result of the applied force and require retightening.

SUMMARY

The present disclosure relates to a system and method for inserting an intramedullary (IM) nail. An IM nail insertion assembly includes an IM nail extending longitudinally from a proximal end to a distal end. A proximal portion of the IM nail has an internal threading. The IM nail insertion assembly also includes a connecting screw extending longitudinally from a proximal end to a distal end. A distal portion of the connecting screw has an external threading for engaging the internal threading of the IM nail. One of the proximal portion of the IM nail and the distal portion of the connecting screw has a feature to resist a disengagement of the proximal portion from the distal portion.

In an embodiment, the feature is a portion of the external threading of the connecting screw having a first pitch different from a remainder of the external threading having a second pitch.

In an embodiment, the first pitch is greater than the second pitch.

In an embodiment, the second pitch is greater than the first pitch.

In an embodiment, the feature is a portion of the internal threading of the IM nail having a first pitch different from a remainder of the internal threading having a second pitch.

In an embodiment, the feature is a portion of the external threading of the connecting screw forming a plurality of detents different from one another.

In an embodiment, each of the detents extends radially from a middle portion of the external threading.

In an embodiment, the portion of the external threading forms two detents.

In an embodiment, the feature is a portion of the internal threading of the IM nail forming a plurality of detents different from one another.

In an embodiment, each of the detents extends radially from a middle portion of the internal threading.

In an embodiment, the portion of the internal threading forms one detent.

In an embodiment, the connecting screw is cannulated.

In an embodiment, the IM nail insertion assembly further includes an insertion handle extending from a proximal end to a distal end; and a sleeve extending longitudinally from a proximal end to a distal end, the proximal end of the sleeve sized and shaped to receive the proximal end of the connecting screw therein. The proximal end of the sleeve is rigidly fixed to the distal end of the insertion handle.

In an embodiment, the sleeve further includes a lumen sized and shaped to receive a shaft of the connecting screw.

In an embodiment, the IM nail insertion assembly further includes a screwdriver extending from a proximal end to a distal end, the screwdriver having a tip at the distal end and a handle at the proximal end. The tip is sized and shaped to engage a recess in the proximal end of the connecting screw.

In an embodiment, the tip is hexagonal for engaging a correspondingly shaped hexagonal recess in the proximal end of the connecting screw.

In an embodiment, the IM nail insertion assembly further includes a tab extending radially from the proximal end of the connecting screw, the tab biased toward a non-deformed state engaging the proximal end of the sleeve.

In an embodiment, the IM nail is made of a titanium alloy.

In an embodiment, the connecting screw is made of a stainless-steel alloy.

The present disclosure also relates to a method which includes inserting an IM nail insertion assembly into a medullary canal, the IM nail insertion assembly including an IM nail, a proximal portion of the IM nail having an internal threading, a connecting screw, a distal portion of the connecting screw having an external threading for engaging the internal threading of the IM nail, and one of the proximal portion of the IM nail and the distal portion of the connecting screw having a feature to resist a disengagement of the proximal portion from the distal portion; inserting a tip of a screwdriver into a recessed portion of a head of the connecting screw; and rotating the screwdriver in a first direction to engage the external threading of the connecting screw with the internal threading of the IM nail.

In an embodiment, the method further includes rotating the screwdriver in a second direction opposite of the first direction; removing the connecting screw; and placing an end cap on a proximal end of the IM nail.

BRIEF DESCRIPTION

FIG. 1 shows a system for performing an intramedullary (IM) nail insertion procedure according to various exemplary embodiments of the present disclosure FIG. 2 shows a magnified view of the system of FIG. 1

DETAILED DESCRIPTION

Figure 3A:
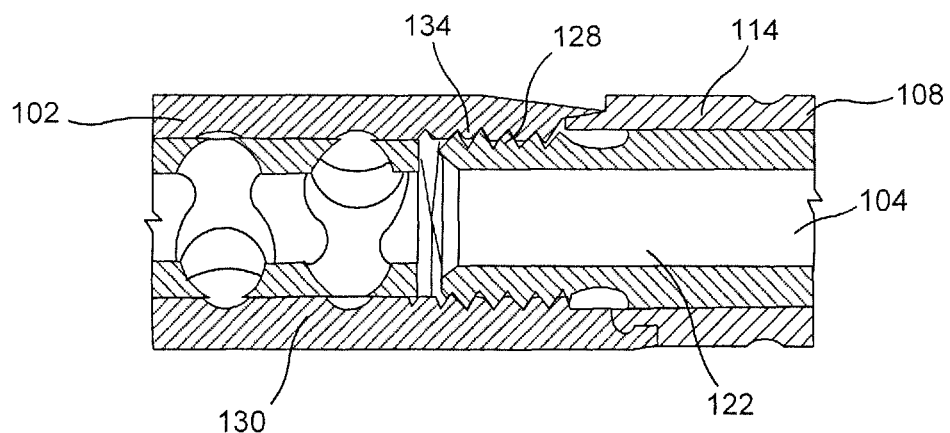
FIG. 3a shows a magnified view of a proximal end of the IM nail engaged with a distal end of the connecting screw of the system of FIG. 1.

The present disclosure may be further understood with reference to the following description and the appended drawings, wherein like elements are referred to with the same reference numerals. The exemplary embodiments describe connecting screws and/or intramedullary (IM) nails having features to resist disengagement or loosening therebetween during nail insertion. The connecting screws and IM nails described herein may be implemented in a system for inserting an IM nail. It should be noted that the terms "proximal" and "distal," as used herein are intended to refer to a direction toward (proximal) and away from (distal) a user of the device.

FIGS. 1-3b show a system 100 for performing an intramedullary (IM) nail insertion procedure according to various exemplary embodiments of the present disclosure. The system 100 includes an intramedullary (IM) nail 102 according to a first embodiment sized and shaped to be inserted into a medullary canal to repair a bone defect. The IM nail 102 insertion is implemented with a connecting screw 104 according to a first embodiment that is coupled to the IM nail 102 during insertion and detached therefrom when the IM nail 102 is fully inserted. During the insertion procedure the connecting screw 104 is further coupled to an insertion handle 106 that is gripped by the operating physician. Forces, e.g., hammering forces, are applied to the insertion handle 106 to push the attached IM nail 102 into the medullary canal as would be understood by those skilled in the art. The applied forces may be significant and can stress the connection between the IM nail 102 and the connecting screw 104.

Due to the magnitude of the forces applied to the system 100 and to facilitate the set-up of the various components, various elements involved are connected in multiple ways in part to maintain a secure connection during the insertion procedure. An initial connection is made between the insertion handle 106 and the IM nail 102 via a sleeve 108 extending from a distal end of the insertion handle 106. The sleeve 108 has a proximal end 112 rigidly connected to the distal end of the insertion handle 106. The sleeve 108 is part of the insertion handle 106 and is rigidly fixed at its proximal end 112, thus the sleeve 108 cannot be disassembled from the handle 106. In the present embodiment, a distal end 114 of the sleeve 108 has a feature shaped to snap-lock into a correspondingly shaped feature at a proximal end 130 of the IM nail 102. For example, the proximal end 130 of the IM nail 102 may have a protrusion extending radially inward that engages a correspondingly sized and shaped recess in the distal end 114 of the sleeve 108. However, other attachment mechanisms between the sleeve 108 and the IM nail 102 may be used.

The sleeve 108 has a hollow interior sized and shaped to receive a longitudinal shaft 124 of the connecting screw 104. Thus, once the sleeve 108 and the IM nail 102 are initially attached to one another, the distal end 122 of the connecting screw 104 is inserted into the proximal end 112 of the sleeve 108 and extended through the length of the sleeve 108 to engage the proximal end 130 of the IM nail 102, as described below, to more securely connect the IM nail 102 to the sleeve 108. The proximal end 112 of the sleeve 108 has an increased diameter relative to the remainder of the sleeve 108, the proximal end 112 having a recessed portion 116 to receive a head 126 of the connecting screw 104 so that the head 126 is seated in the recessed portion 116 when the connecting screw 104 and the IM nail 102 are coupled.

The connecting screw 104 is cannulated, to enable the insertion of the IM nail 102 and the insertion handle 106 over a reaming rod. The connecting screw 104 has a channel extending throughout the length of the connecting screw 104 from a proximal end 120 to a distal end 122. The distal end 122 has an external threaded portion 128 for engaging a correspondingly threaded inner surface 134 on the proximal end 130 of the cannulated IM nail 102, as seen in FIG. 3a.

Figure 3B:
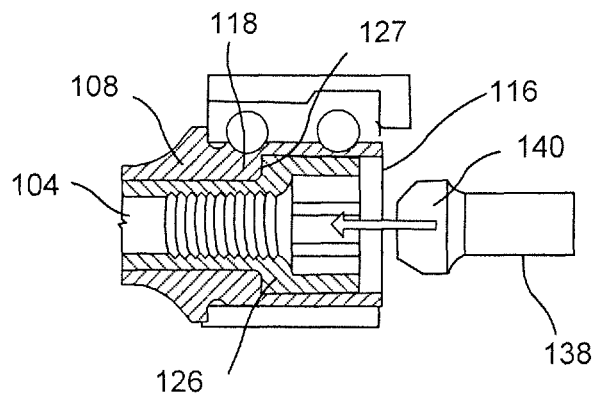
FIG. 3b shows a magnified view of the proximal end of the connecting screw of the system of FIG. 1.

The connecting screw 104 is inserted through the sleeve 108 and a T-arm screwdriver 110 is used to thread the distal end 122 of the connecting screw 104 into the proximal end 130 of the IM nail 102. The T-arm 110 has a longitudinal shaft 138 extending from a proximal handle 136 to a distal tip 140, the tip 140 sized and shaped to engage the countersunk head 126 of the connecting screw 104. In this embodiment, the tip 140 is hexagonal for engaging a correspondingly shaped hexagonal recess in the head 126 of the connecting screw 104, however, other shapes for the tip 140 of the T-arm 110 and the head 126 may be used. The T-arm screwdriver 110 is used to tighten the connecting screw 104 until a distal face 127 of the head 126 of the connecting screw 104, i.e., the portion of the head 126 extending radially between the outer surface of the head 126 and the shaft 124, engages a proximal shoulder 118 of the recessed portion 116 of the sleeve 108, i.e., the portion of the sleeve 108 extending radially between the inner surface of the recessed portion 116 and the inner surface of the sleeve 108, as shown in FIG. 3b. This tightening may cause a compressive force between the connecting screw 104 and the sleeve 108 that coincides with the engagement of the connecting screw 104 and the IM nail 102 via the threaded portions 128, 134, further strengthening the connections between the components.

When the connecting screw 104 and the IM nail 102 have been joined, the operating physician may proceed to drive the distal end 132 of the IM nail 102 into the medullary canal. As would be understood by those skilled in the art, the connection between the distal end 122 of the connecting screw 104 and the proximal end 130 of the IM nail 102 may be stressed during this procedure. To prevent a loosening of the connection, which would typically require a retightening of the connection with the T-arm 110 in the middle of the insertion procedure, the system 100 according to various exemplary embodiments includes features to provide a more secure connection that resists such a loosening effect during the insertion procedure. The IM nail 102 in the exemplary embodiments may be made of a titanium alloy, for example, TAN or TAV. The connecting screw 104 in the above embodiment, as well as connecting screws in the following embodiments, may be made of a stainless steel alloy.

Figure 4:
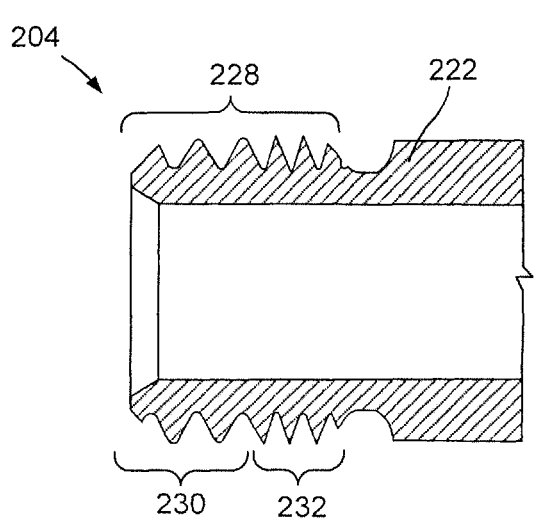
FIG. 4 shows a distal end of a connecting screw according to a second embodiment.

FIG. 4 shows a distal end 222 of a connecting screw 204 according to a second embodiment. The connecting screw 204 may be substantially similar to the connecting screw 104 described above, with the exception of the distal end 222. In this second embodiment, the distal end 222 has a threaded portion 228 with a variable pitch, including a first thread 230 extending from the distal-most point of the threaded portion 228 to a transition approximately midway through the threaded portion 228 and a second thread 232 extending from the transition to the proximal-most point of the threaded portion 228. Those skilled in the art will understand that the pitch of a thread relates to the angle of the helix along which the thread extends (i.e., an angle between the axial progression of the helix and the axis of the cylinder around which it wraps) and that a smaller pitch represents a larger helical angle so that the threads of a smaller pitch are closer to one another than are the threads of a larger pitch.

The first thread 230 has a first pitch that corresponds to the pitch of the interior threaded portion 134 of the IM nail 102, while the second thread 232 has a second pitch that is smaller than that of the first thread 230 and interior threaded portion 134 so that the second thread 232 generates interference with the interior threaded portion 134. A ratio between the first pitch of the first thread 230 and the second pitch of the second thread 232 being from 0.5 to 0.99. As the threaded portion 228 of the connecting screw 204 is advanced along the threaded portion 134 of the IM nail 102 the second (smaller) thread 232 engages the threaded portion 134 of the IM nail 102.

Due to the differing pitches, one or both of the engaging threads will deform causing the distal end 222 of the connecting screw 204 and the proximal end 130 of the IM nail 102 to become more tightly joined to one another in a manner that resists loosening during the insertion procedure. Despite the deformation caused by the tightening, once the IM nail 102 has been fully inserted, the engaging threads may be subsequently disengaged by rotating the connecting screw 204 in the direction opposite the tightening direction.

If the threaded portion 134 of the IM nail 102 is deformed during the advancement of the connecting screw 204, the first thread 230 of the connecting screw 204 will engage the deformed threaded portion 134 and may substantially counteract the deformation—that is, the engagement of the first thread 230 with the interior threaded portion 134 will retap and correct the threading of the interior portion 134. Thus, if and when further elements are attached to the threaded portion 134 of the IM nail 102, e.g. an end cap, the end cap will not encounter significant resistance when tightened thereon. Accordingly, if the first thread 230 matches with the threaded portion 134 of the IM nail 102, the threaded portion 134 of the IM nail 102 will not deform and thus, the endcap will have a tight fit within the IM nail 102.

Figure 5:
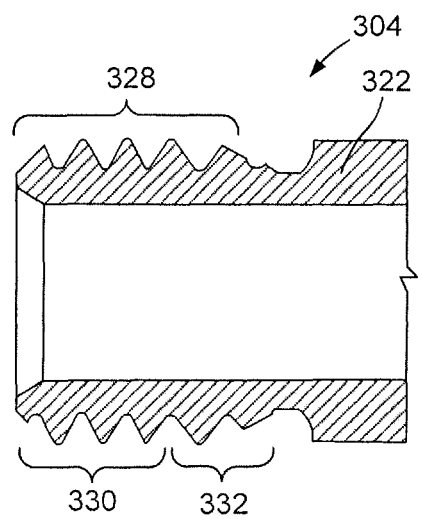
FIG. 5 shows a distal end of a connecting screw according to a third embodiment.

FIG. 5 shows a distal end 322 of a connecting screw 304 according to a third embodiment. The connecting screw 304 may be substantially similar to either of the connecting screws 104, 204 described above with the exception of the distal end 322. In this third embodiment, the distal end 322 has a threaded portion 328 with a variable pitch, including a first thread 330 extending from the distal-most point of the threaded portion 328 to a transition approximately midway through the threaded portion 328 and a second thread 332 extending from the transition to the proximal-most point of the threaded portion 328, similar to the connecting screw 204 of the first embodiment.

However, in the third embodiment, the first thread 330 has a first pitch that corresponds to the pitch of the interior threaded portion 134 of the IM nail 102, while the second thread 332 has a pitch that is larger than that of the first thread 330 and interior threaded portion 134. In a manner similar to that of the connecting screw 204 described above, as the threaded portion 328 of the connecting screw 304 is advanced along the threaded portion 134 of the IM nail 102 the second thread 332 engages the threaded portion 134 of the IM nail 102. A ratio between the first pitch of the first thread 330 and the second pitch of the second thread 332 being from 1.01 to 2.

Due to the differing pitches, one or both of the engaging threads will deform, the deformation causing the distal end 322 of the connecting screw 304 and the proximal end 130 of the IM nail 102 to become tightly joined together and resist loosening during the insertion procedure. If the threaded portion 134 of the IM nail 102 was deformed during the advancement of the connecting screw 304, the first thread 330 of the connecting screw 304 will engage the deformed threaded portion 134 and substantially correct the deformation. Thus, if and when further elements are attached to the threading 134 of the IM nail 102, e.g. an end cap, the end cap will not encounter significant resistance when tightened thereon.

By adjusting the pitch on the proximal end of the threading, rather than the distal end, only a proximal portion of the corresponding threading of the IM nail 102 will potentially deform when the connecting screw is advanced, rather than the entirety of the threading. In alternate embodiments, connecting screws are provided having the smaller/larger pitches of connecting screws 204, 304, but without the distal threading corresponding to the threading of the IM nail 102. Thus, when the connecting screws are threaded into the IM nail 102, only the smaller/larger pitched thread of the connecting screws engages the threaded portion 134 of the IM nail 102 and the distal portion of the threaded portion 134 remains unengaged.

Figure 6:
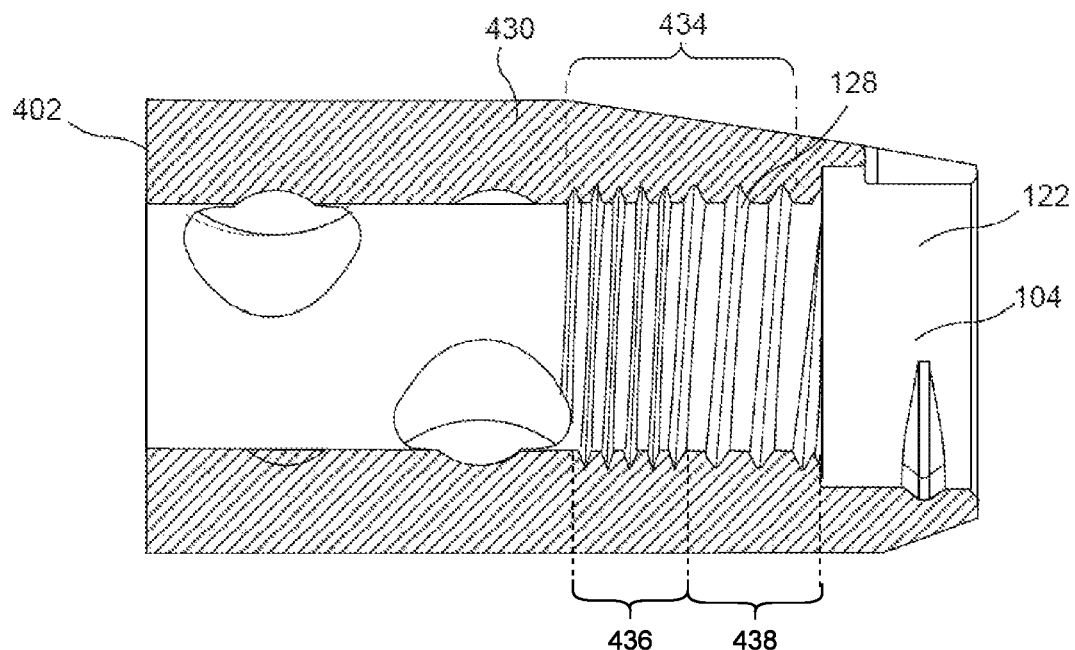
FIG. 6 shows a proximal end of an IM nail according to a second embodiment.

The principle described above with respect to connecting screws 204, 304 may be implemented instead at the IM nail 102. Specifically, the connecting screw 104, having a uniform pitch for its threaded portion 128, may be used with an IM nail having a variable pitch for its threaded portion. In these embodiments, a distal portion of the IM nail threading has the smaller or larger pitch, causing either the threading 128 of the connecting screw 104 or the distal threading of the IM nail to deform as the connecting screw 102 is advanced FIG. 6 shows a proximal end 430 of an IM nail 402 according to a second embodiment. The IM nail 402 may be substantially similar to the IM nail 102 described above with the exception of the proximal end 430. The IM nail 402 has a threaded portion 434 with a variable pitch, including a first thread 436 extending from the distal-most point of the threaded portion 434 to a transition approximately midway through the threaded portion 434 and a second thread 438 extending from the transition to the proximal-most point of the threaded portion 434. The first thread 436 has a first pitch that is smaller than that of the second thread 438, the second thread 438 having a second pitch that corresponds to the pitch of the exterior threaded portion 128 of the connecting screw 104.

Figure 7:
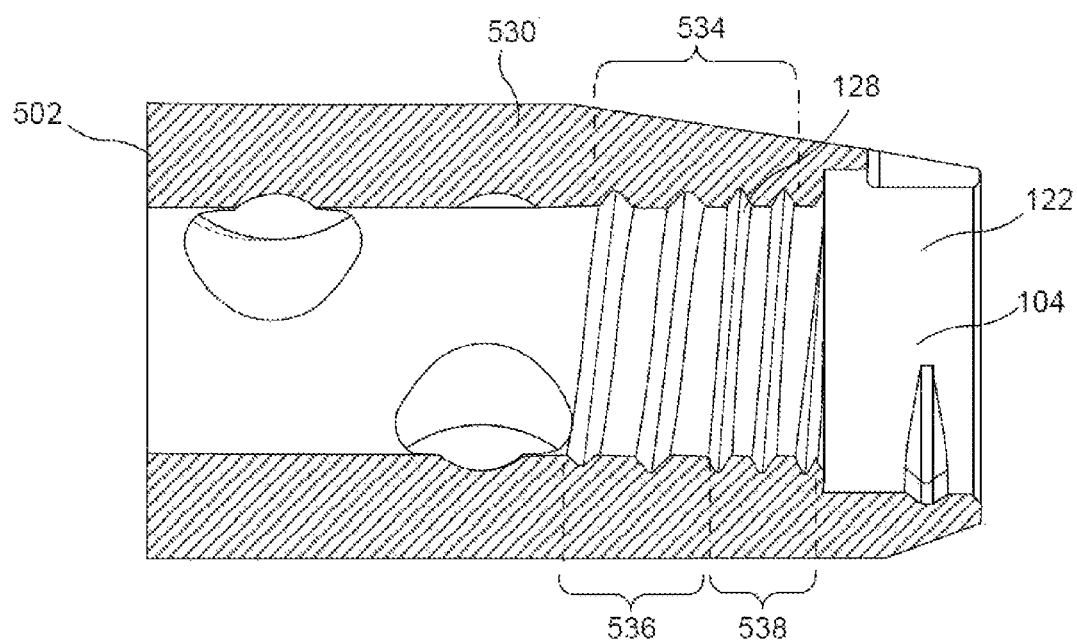
FIG. 7 shows a proximal end of an IM nail according to a third embodiment.

FIG. 7 shows a proximal end 530 of an IM nail 502 according to a third embodiment for use in the system 100 of FIG. 1. The IM nail 502 may be substantially similar to the IM nails 102 or 402 described above with the exception of the proximal end 530. The IM nail 502, similar to the IM nail 402, has a threaded portion 534 with a variable pitch, including a first thread 536 extending from the distal-most point of the threaded portion 534 to a transition approximately midway through the threaded portion 534 and a second thread 538 extending from the transition to the proximal-most point of the threaded portion 534. The first thread 536 has a first pitch that is larger than that of the second thread 538, the second thread 538 having a second pitch that corresponds to the pitch of the exterior threaded portion 128 of the connecting screw 104.

Figure 8:
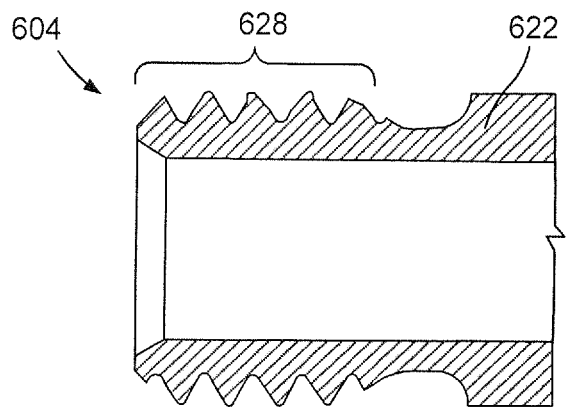
FIG. 8 shows a distal end of a connecting screw according to a fourth embodiment.
Figure 9:
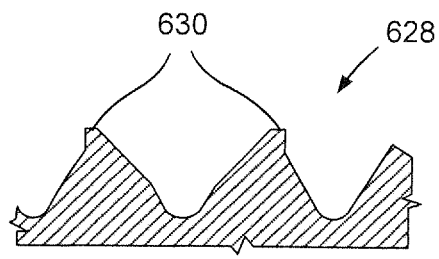
FIG. 9 shows a magnified view of the connecting screw of FIG. 8.

FIG. 8 shows a distal end 622 of a connecting screw 604 according to a fourth embodiment. The connecting screw 604 may be substantially similar to any of the connecting screws 104, 204, 304 described above, with the exception of the distal end 622. In this fourth embodiment, the distal end 622 has a threaded portion 628 including a detent 630 at two locations on the threaded portion 628, as shown in FIG. 9. The two detents 630 extend radially from a middle portion of the threading and are shaped differently from the remainder of the threading.

Specifically, the threading is deformed axially so that gaps between adjacent portions of the threading are either narrower or wider. Thus, the detents 630 will cause mechanical interference with the threaded portion 134 of the IM nail 102 when the IM nail 102 and the connecting screw 604 are screwed together. Although the threaded portion 628 shown in FIG. 8 has two detents 630, more or fewer detents may be used. In a similar manner to the connecting screws 204, 304 described above, when the distal end 622 is threaded into the proximal end 130 of the IM nail 102, the detents 630 engage the threaded portion 134 of the IM nail 102 so that the mechanical interference between more tightly locks the connecting screw 604 and the IM nail 102 to one another. The detents 630 may be on a proximal portion of the threaded portion of 628 in order to interfere only with a proximal portion of the threaded portion 134 of the IM nail, thus, if and when further elements are attached to the threaded portion 134 of the IM nail 102, e.g. an end cap, the end cap will have a tight fit with the IM nail 102.

Figure 10:
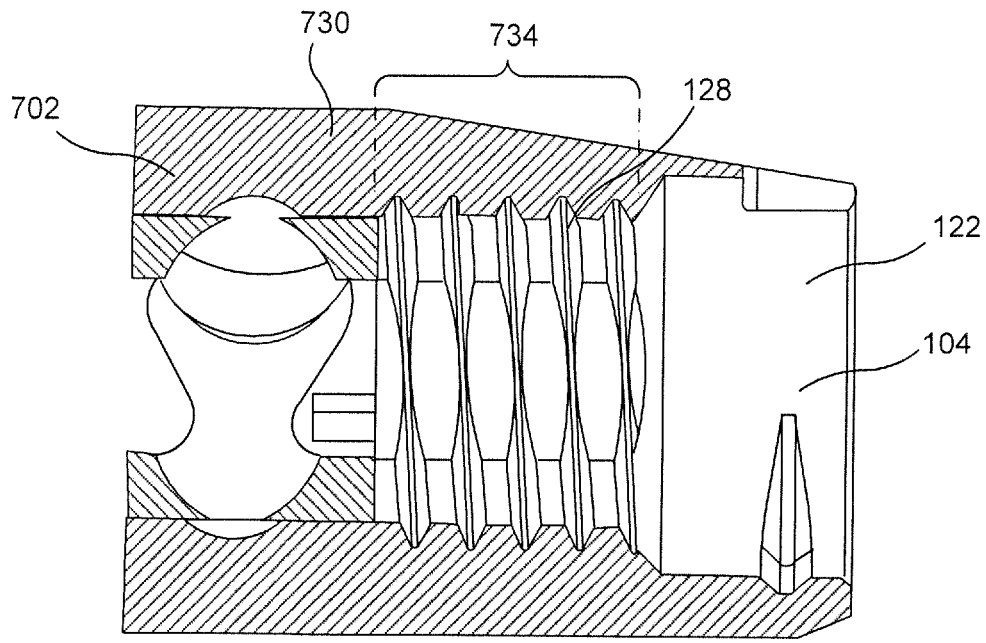
FIG. 10 shows a proximal end of an IM nail according to a fourth embodiment.
Figure 11:
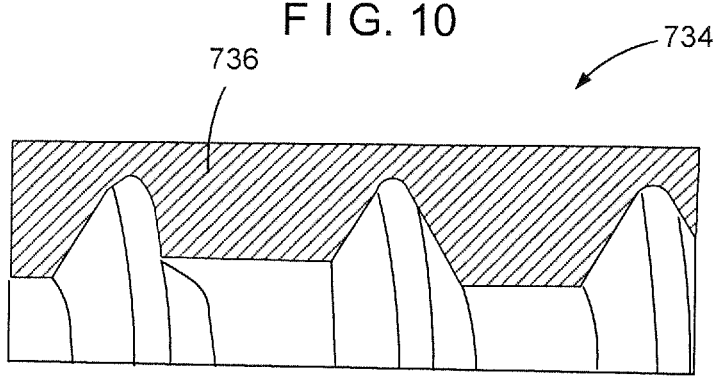
FIG. 11 shows a magnified view of the IM nail of FIG. 10.

FIG. 10 shows a proximal end 730 of an IM nail 702 according to a fourth embodiment. The IM nail 702 may be substantially similar to the IM nails 102, 402, 502 described above with the exception of the proximal end 730. In this fourth embodiment, the IM nail 702 has a threaded portion 734 including a detent 736 extending laterally from a middle portion of the threading. The detent 736 is a portion of the threading that is deformed relative to the remainder of the threading. Thus, due to the detent 736, the shape of the threading of the threaded portion 734 differs from the shape of the gaps between the turns of the threading of the threaded portion 128 and, as these parts are screwed together, this difference in shape generates a mechanical interference between the threaded portion 128 of the connecting screw 104 and the IM nail 702 that resists loosening during the implantation of the IM nail 702. Although the threaded portion 734 has a single detent, as shown in FIG. 11, more detents may be used.

In addition to the mechanisms described above at either the distal end of a connecting screw or the proximal end of an IM nail, a further mechanism may be implemented at the proximal end of a connecting screw to resist disengagement of the tight connection between the connecting screw and an IM nail.

Figure 12:
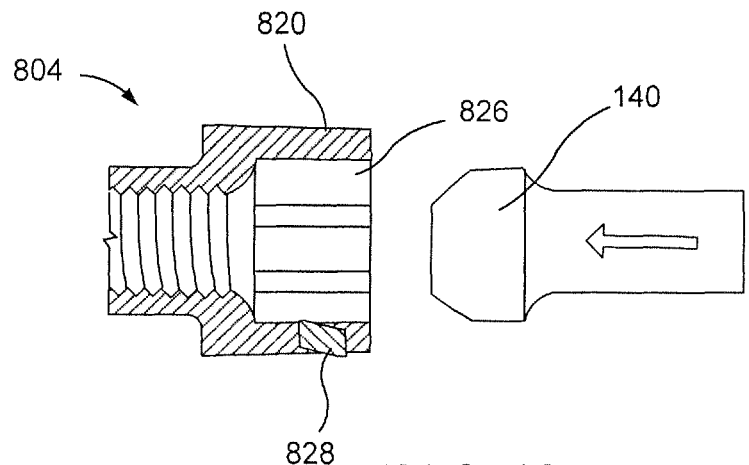
FIG. 12 shows a proximal end of a connecting screw according to a fifth embodiment.
Figure 13:
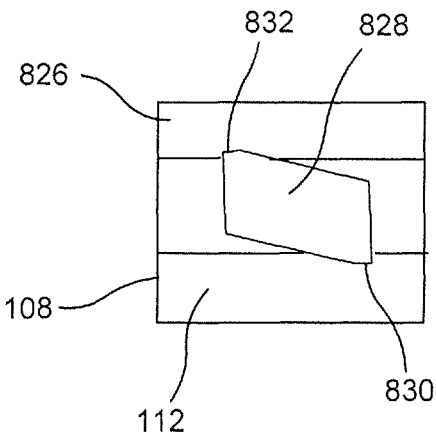
FIG. 13 shows a magnified view of a tab of the proximal end of the connecting screw shown in FIG. 12 in a non-deformed state.

FIG. 12 shows a proximal end 820 of a connecting screw 804 according to a fifth embodiment. The connecting screw 804 may be substantially similar to the connecting screw 104 described above with the exception of the proximal end 820. In this embodiment, the countersunk head 826 of the proximal end 820 has a deformable tab 828 extending radially through the head 826. In a natural, i.e., non-deformed state, the tab 828 is oriented so that an outer portion 830 of the tab 828, e.g. a corner, projects radially outward relative to the outer surface of the head 826, as shown in FIG. 13. Thus, when the connecting screw 804 is inserted in the sleeve 108 of the insertion handle 106, the outer portion 830 engages the proximal end 112 of the sleeve 108.

This engagement acts to prevent movement, e.g. rotation, of the connecting screw 804 relative to the sleeve 108. For example, during the insertion procedure, stresses generated by the insertion forces may act to dislodge the connecting screw 804 from the IM nail 102 or the sleeve 108. The tab 828, in its non-deformed state, provides a force resisting relative movement, e.g. rotation, between the connecting screw 804 and the sleeve 108, which further resists movement between the connecting screw 804 and the IM nail 102, considering the rigid connection between the sleeve 108 and the IM nail 102 described above.

Figure 14:
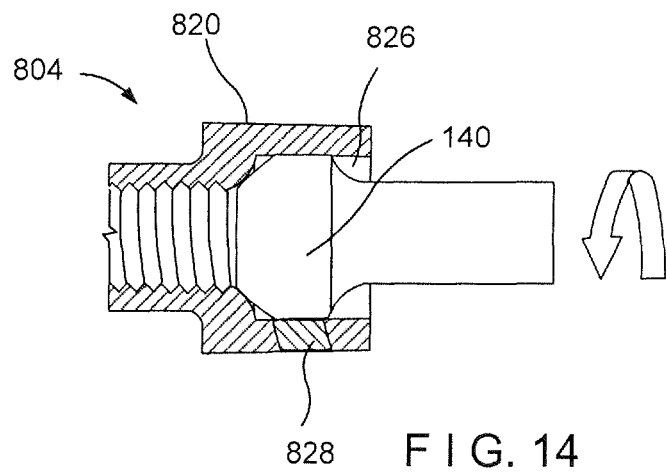
FIG. 14 shows the proximal end of the connecting screw of FIG. 12 with a screwdriver tip inserted therein and the tab in a deformed state.

In its non-deformed state, the tab 828 also has an inner portion 832, i.e. the opposing corner of the outer portion 830, projecting radially inward relative to the inner surface of the head 826. However, when the tip 140 of the T-arm 110 is engaged in the recess of the countersunk head 826 of the connecting screw 804, the tip 140 forces the inner portion 832 radially outward and the tab 828 deforms under the pressure from the tip 140. The deformation causes the tab 828 to straighten out, such that the outer portion 830 no longer engages the proximal end 112 of the sleeve 108, as shown in FIG. 14. Thus, the connecting screw 804 may be rotated relative to the sleeve 108 when the tip 140 of the T-arm 110 is inserted in the countersunk head 826. This allows the connecting screw 804 to be threaded into the IM nail 102 at the outset of the nail insertion procedure and unthreaded from the IM nail 102 at the end of the insertion procedure without the tab 828 causing interference with the sleeve 108. In other words, the connecting screw 804 is rotatable relative to the sleeve 108 when the tip 140 of the T-arm 110 is inserted in countersunk head 826, and when the T-arm 110 is withdrawn the tab 828 resists rotation, providing a more secure connection between the connecting screw 804 and the IM nail 102.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

The invention claimed is:

1. An intramedullary (IM) nail insertion assembly, comprising:
   an insertion handle extending from a proximal end to a distal end; and
   an IM nail extending longitudinally from a proximal end to a distal end, a proximal portion of the IM nail having an internal threading;
   a connecting screw extending longitudinally from a proximal end to a distal end, a distal portion of the connecting screw having an external threading for engaging the internal threading of the IM nail, the connecting screw including a tab extending radially from the proximal end of the connecting screw; and
   a sleeve extending longitudinally from a proximal end to a distal end, the proximal end of the sleeve sized and shaped to receive the proximal end of the connecting screw therein, wherein the proximal end of the sleeve is rigidly fixed to the distal end of the insertion handle, and wherein the tab is biased toward a non-deformed state in which the tab extends outward from the connecting screw to engage the proximal end of the sleeve preventing rotation of the connecting screw relative to the sleeve, the tab being configured to be moved to a deformed state in which the tab is moved inward out of engagement with the proximal end of the sleeve permitting rotation of the connecting screw relative to the sleeve, wherein one of the internal threading of the proximal portion of the IM nail and the external threading of the distal portion of the connecting screw has a feature configured to generate mechanical interference between the internal threading and the external threading by deforming of one of the internal threading and the external threading to resist a disengagement of the proximal portion from the distal portion.

2. The IM nail insertion assembly of claim 1, wherein the feature is a portion of the external threading of the connecting screw having a first pitch different from a remainder of the external threading having a second pitch.

3. The IM nail insertion assembly of claim 2, wherein the first pitch is greater than the second pitch.

4. The IM nail insertion assembly of claim 2, wherein the second pitch is greater than the first pitch.

5. The IM nail insertion assembly of claim 1, wherein the feature is a portion of the internal threading of the IM nail having a first pitch different from a remainder of the internal threading having a second pitch.

6. The IM nail insertion assembly of claim 1, wherein the feature is a portion of the external threading of the connecting screw forming a plurality of detents different from one another.

7. The IM nail insertion assembly of claim 6, wherein each of the detents extends radially from a middle portion of the external threading.

8. The IM nail insertion assembly of claim 6, wherein the portion of the external threading forms two detents.

9. The IM nail insertion assembly of claim 1, wherein the feature is a portion of the internal threading of the IM nail forming a plurality of detents different from one another.

10. The IM nail insertion assembly of claim 9, wherein each of the detents extends radially from a middle portion of the internal threading.

11. The IM nail insertion assembly of claim 9, wherein the portion of the internal threading forms one detent.

12. The IM nail insertion assembly of claim 1, wherein the connecting screw is cannulated.

13. The IM nail insertion assembly of claim 1, wherein the sleeve further comprises a lumen sized and shaped to receive a shaft of the connecting screw.

14. The IM nail insertion assembly of claim 1, further comprising:
a screwdriver extending from a proximal end to a distal end, the screwdriver having a tip at the distal end and a handle at the proximal end,
wherein the tip is sized and shaped to engage a recess in the proximal end of the connecting screw.

15. The IM nail insertion assembly of claim 14, wherein the tip is hexagonal for engaging a correspondingly shaped hexagonal recess in the proximal end of the connecting screw.

16. The IM nail insertion assembly of claim 14, wherein the tip of the screwdriver is configured so that, when the tip engages the recess in the proximal end of the connecting screw, the tip of the screwdriver deflects the tab of the connecting screw to the deformed state.

17. The IM nail insertion assembly of claim 1, wherein the 1M nail is made of a titanium alloy.

18. The IM nail insertion assembly of claim 1, wherein the connecting screw is made of a stainless-steel alloy.

19. A method, comprising:
inserting an IM nail insertion assembly into a medullary canal, the IM nail insertion assembly including an IM nail, a proximal portion of the IM nail having an internal threading, an insertion handle including a sleeve extending from a proximal end rigidly connected to the insertion handle and a distal end configured to be coupled to a proximal end of the IM nail;
inserting through the sleeve a connecting screw including a distal portion having an external threading for engaging the internal threading of the 1M nail and a proximal end formed as a head, wherein the connecting screw includes a tab extending radially from the proximal end of the connecting screw, the tab being biased toward a non-deformed state in which the tab extends outward from the screw to engage the sleeve preventing rotation of the connecting screw relative to the sleeve, wherein one of the internal threading of the proximal portion of the IM nail and the external threading of the distal portion of the connecting screw having includes a feature configured to generate mechanical interference between the internal threading and the external threading, which resists a disengagement of the proximal portion from the distal portion;
inserting a tip of a screwdriver into a recessed portion of a head of the connecting screw to deflect the tab of the connecting screw to a deformed state in which the tab is moved radially inward out of engagement with the proximal end of the sleeve permitting rotation of the connecting screw relative to the sleeve; and
rotating the screwdriver in a first direction to engage the external threading of the connecting screw with the internal threading of the IM nail so that the mechanical interference deforms one of the internal threading and the external threading to tightly join the connecting screw to the IM nail.

20. The method of claim 19, further comprising:
re-inserting the tip of the screwdriver into the recessed portion of the head of the connecting screw to deflect the tab of the connecting screw to the deformed state;
rotating the screwdriver in a second direction opposite of the first direction;
removing the connecting screw; and
placing an end cap on a proximal end of the IM nail.

* * * * *

UNITED STATES PATENT AND TRADEMARK OFFICE
CERTIFICATE OF CORRECTION

PATENT NO. : 11,553,933 B2
APPLICATION NO. : 16/736400
DATED : January 17, 2023
INVENTOR(S) : Spreiter et al.

It is certified that error appears in the above-identified patent and that said Letters Patent is hereby corrected as shown below:

In the Claims

Claim 19, Column 10, Line 20:
"ing the internal threading of the 1M nail and a proximal" should read "ing the internal threading of the IM nail and a proximal"

Signed and Sealed this
Twenty-eighth Day of February, 2023

Katherine Kelly Vidal
*Director of the United States Patent and Trademark Office*